United States Patent
Nijkamp et al.

(10) Patent No.: US 6,960,565 B2
(45) Date of Patent: Nov. 1, 2005

(54) COMPOUND FOR INHIBITING THE INFLUX OF POLYMORPHONUCLEAR LEUKOCYTES (PMNS) IN A TISSUE, ITS SELECTION, PHARMACEUTICAL COMPOSITIONS AND USE

(75) Inventors: Franciscus Petrus Nijkamp, Houten (NL); Rosswell Robert Pfister, Harpersville, AL (US); Jeffrey Lynn Haddox, Birmingham, AL (US); James Edwin Blalock, Vestavia Hills, AL (US); Matteo Villain, Gorla Minore (IT)

(73) Assignee: Fornix Biosciences N.V., Lelystad (NL)

( * ) Notice: Subject to any disclaimer, the term of this patent is extended or adjusted under 35 U.S.C. 154(b) by 0 days.

(21) Appl. No.: 10/712,985

(22) Filed: Nov. 13, 2003

(65) Prior Publication Data

US 2004/0176304 A1 Sep. 9, 2004

Related U.S. Application Data

(63) Continuation of application No. 09/958,049, filed as application No. PCT/NL00/00225 on Apr. 6, 2000, now abandoned.

(30) Foreign Application Priority Data

Apr. 6, 1999 (NL) .............................................. 1011737

(51) Int. Cl.[7] .......................... A61K 38/06; A61P 29/00; C07K 5/08; C07K 5/097; C07K 14/00

(52) U.S. Cl. ........................... 514/13; 514/18; 530/325; 530/331; 530/332

(58) Field of Search ................................ 530/325, 331, 530/332; 514/13, 18

(56) References Cited

U.S. PATENT DOCUMENTS

| | | | | |
|---|---|---|---|---|
| 5,932,217 A | * | 8/1999 | Tuomanen et al. | 424/185.1 |
| 6,013,674 A | * | 1/2000 | Morin, Jr. et al. | 514/621 |
| 6,310,041 B1 | | 10/2001 | Haddox et al. | 514/12 |
| 6,489,300 B1 | * | 12/2002 | Thorsett et al. | 514/19 |
| 2001/0006656 A1 | * | 7/2001 | Harlan et al. | 424/400 |
| 2002/0172679 A1 | * | 11/2002 | Ringler et al. | 424/146.1 |

OTHER PUBLICATIONS

Haddox, J.L., et al., entitled "Bioactivity of Peptide Analogs of the Neutrophil Chemoattractant N–Acetyl–Proline–Glycine–Proline," Investigative Ophthalmology and Visual Science; Sep. 1999; 40(10): 2427–9.

Pfister, R.R., et al., entitled "Injection of Chemoattractants into Normal Cornea A Model of Inflammation After Alkali Injury," Investigative Ophthalmology and Visual Science; Aug. 1998; 39(9): 1744–50.

Pfister, R.R., et al., entitled "A Neutrophil Chemoattractant is Released from Cellular and Extracellular Components of the Alkali–Degraded Cornea and Blood," Investigative Ophthalmology and Visual Science; Jan. 1996; 37(1): 230–7.

Blalock, J.E., entitled "Genetic Origins of Protein Shape and Inteaction Rules," Nature Medicine; 1995 (1): 876–878.

(Continued)

*Primary Examiner*—Jeffrey Edwin Russel
(74) *Attorney, Agent, or Firm*—Amster, Rothstein & Ebenstein LLP

(57) ABSTRACT

The invention relates to a compound suitable for inhibiting the influx of polymorphonuclear leukocytes (PMNs) into a tissue involved in a chronic inflammatory disease. The compound according to the invention is capable of forming a complex with N-acetyl-Pro-Gly-Pro. The invention also relates to a method of selecting such a compound, a pharmaceutical composition and an application of the compound.

8 Claims, 1 Drawing Sheet

OTHER PUBLICATIONS

Pfister, E.A., entitled "Identification and Synthesis of Chemotactic Tripeptides From Alkali–Degraded Whole Cornea A Study of N–Acetyl–Proline–Glycine–Proline and N–Methyl–Proline–Glycine–Proline," Investigative Ophthalmology and Visual Science; Jun. 1995; 36(7): 1306–16.

Laskin D., et al., entitled "Chemotactic Activity of Collagen–Like Polypeptides for Human Peripheral Blood Neutrophils," Journal of Leukocyte Biology Mar. 1986; 39(3): 255–66.

* cited by examiner

COMPOUND FOR INHIBITING THE INFLUX OF POLYMORPHONUCLEAR LEUKOCYTES (PMNS) IN A TISSUE, ITS SELECTION, PHARMACEUTICAL COMPOSITIONS AND USE

This application in a continuation of U.S. patent application Ser. No. 09/958,049, filed Apr. 4, 2002, now abandoned which is a national stage entry under 35 U.S.C. §371 of PCT International Application No. PCT/NL00/00225, filed Apr. 6, 2000, which claims priority of Dutch Patent Application No. NL 1011737, filed Apr. 6, 1999, the contents of all of which are incorporated herein by reference in their entirety.

Compound for inhibiting the influx of polymorphonuclear leukocytes (PMNs) in a tissue, method of selecting such a compound, a pharmaceutical composition, and an application of the compound The present invention relates to a compound suitable for inhibiting the influx of polymorphonuclear leukocytes (PMNs) into a tissue involved in a chronic inflammatory disease in a mammal, which compound, in the presence of equimolar amounts of a) N-acetyl-Pro-Gly-Pro ("N-AcPGP"), b) a compound designated as 4RTR with the formula I

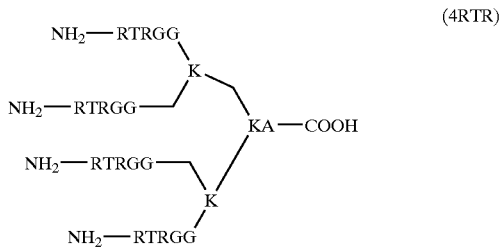

(4RTR)

which is capable of forming a complex with N-AcPGP, and c) the compound, inhibits complex formation between N-AcPGP and 4RTR by at least 10% due to N-AcPGP being bound by the compound.

As the person skilled in the art knows, in the formula 4RTR, R, T, G, K and A stand for arginine, threonine, glycine, lysine, and alanine. Influx of polymorphonuclear leukocytes (PMNs), such as neutrophilic and eosinophilic granulocytes, plays a role with chronic inflammatory diseases. In the present application chronic inflammatory diseases are understood to include all inflammatory diseases induced by prolonged exposure to a foreign substance or where no exposure to a foreign substance is involved. These include in particular inflammatory disorders of the lungs, joints, and bowels, among which autoimmune diseases, (severe) asthma and lung emphysema. With such chronic inflammatory diseases of this kind, PMNs migrate from peripheral blood into a tissue where they cause damage to said tissue. Normally, the influx of PMNs should occur only to combat an infection with potentially harmful microorganisms. The influx of PMNs causes, due to the secretion of additional signalling substances such as leukotrienes, an influx of other inflammatory cells, thus increasing the damage to the tissue. A compound binding N-AcPGP, a signal substance activating PMNs, significantly inhibits the pre-activation of PMNs and consequently the influx of the neutrophilic granulocytes. The phrase "as a result of N-AcPGP being bound by the compound" means that the compound is capable of forming a complex with N-AcPGP but not with 4RTR. Using well-known techniques, such as a microcaloric technique, the person skilled in the art is quite well able to establish that such a complex has been formed (Ref. 1 and 2).

Preferably, the compound inhibits the formation of the complex by at least a 25%, preferably by at least 50%, more preferably by at least 70%, and most preferably by at least 90%.

Such compounds are more effective and, as a smaller quantity is required for a treatment, they are potentially also more interesting from an economic point of view.

According to the first embodiment the compound is a peptide.

The use of a peptide or a compound comprising a peptide, such as RTR or its oligomers, increases the chance of biological compatibility, as its decomposition products comprise natural amino acids.

If it is desirable that the peptides stay active in the blood longer, the peptide may comprise one or more D-amino acids. According to an alternative embodiment, the compound is a peptidomimetic in which the side chain is located on the nitrogen atom.

Suitable compounds comprise at least two XTR units which are interconnected by means of one or more spacer units. X is any arbitrary amino acid and suitably a natural amino acid such as arginine. Suitably, spacer units each have a length (from RTR unit to RTR unit) of 2 to 10 atoms. To make a spacer it is convenient to use one or more glycine molecules, or synthetic amino acids such as 3-aminopropionic acid. A suitable compound is preferably a branched compound, in which at least three branches comprise an RTR chain. To achieve branching, the compound suitably comprises natural or synthetic di-amino acids (lysine, di-aminoproprionic acid, di-aminobutyric acid). Usually each compound will comprise at the most 100 RTR units, suitably 4 to 6 units. As posited above, instead of the natural amino acids of RTR it is also possible to use the D-variants or variants in which the side chain is located on the nitrogen atom of the backbone. Preferably, a PGP-binding unit, and in particular the compound itself, has a molecular weight of less than 5000, such as <4000.

The invention also relates to a method of screening a number of compounds with respect to their capability to inhibit the formation of a complex between 4RTR and N-AcPGP, screening occurring by means of an assay comprising a competition reaction between i) a compound A to be assayed and ii) a compound B capable of binding N-AcPGP having an equilibrium constant K of $5 \cdot 10^{-5}$ M$^{-1}$ or lower, compound A and compound B being in competition for the binding to a Pro-Gly-Pro (PGP)-comprising compound C, with which the compound B is able to complex, having an equilibrium constant K of $5 \cdot 10^{-5}$ M$^{-1}$ or lower, and wherein a thus assayed compound A is selected having an equilibrium constant K for the reaction between compound A and the PGP-comprising compound C of $10^{-4}$ M$^{-1}$ or lower.

Such a method makes it possible to select compounds, that can be assayed for further pharmacological properties such as in blood half life, toxicity and the like, as is well-known to the person skilled in the art of pharmacology.

Preferably, a compound A is selected having an equilibrium constant K of $10^{-5}$ M$^{-1}$ or below, preferably $10^{-6}$ M$^{-1}$ or below, more preferably $10^{-7}$ M$^{-1}$ or below, and most preferably $10^{-8}$ M$^{-1}$ or below.

Such high affinity compounds A can be used to great advantage for the preparation of a pharmaceutical composition, as will be described below.

Suitably the compound C is N-R-Pro-Gly-Pro ("N-R-PGP"), wherein R is branched or linear alkyl- or acyl group having 1 to 6 carbon atoms, preferably 1 to 2 carbon atoms. A suitable compound C is N-Ac-PGP or N-methyl-Pro-Gly-Pro.

Such PGP-comprising compounds are simple to synthesize and be used for the selection of suitable compounds A. As the compound B for binding the PGP-comprising compound C it is possible to use, for example, 4RTR.

Preferably the assay is a homogenous assay, such as one based on fluorescence (de)polarization or internal energy transfer.

This is a quick and efficient manner of screening a considerable number of compounds and selecting an inhibiting compound.

The invention also relates to compounds suitable for inhibiting the influx of PMNs in a tissue involved in a chronic inflammatory disease in a mammal, which compound E, in the presence of an equimolar amount of N-acetyl-Pro-Gly-Pro ("N-AcPGP"), competes for binding to a PMN and inhibits the binding of N-AcPGP to the PMN by at least 10% as a result of N-AcPGP being bound by the compound, and which compound E does not induce activation of the PMN.

A compound E which does not engage a signal compound such as N-acetyl-Pro-Gly-Pro or N-methyl-Pro-Gly-Pro but its receptor on a neutrophilic granulocyte, is also suitable for inhibiting the influx of PMNs.

Suitably the compound E inhibits binding by at least 25%, preferably by at least 50%, more preferably by at least 70% and most preferably by at least 90%. Again, the compound may be a peptide or peptidomimetic. In that case the above-described advantages concurrently apply.

According to an alternative embodiment the compound is an antibody, preferably a monoclonal antibody, and most preferably a human or humanized monoclonal antibody, or fragments thereof.

With the aid of such antibodies or fragments thereof, it is possible to effectively trap the PGP-comprising signal substance. For long-term activity it is preferred that the antibody be adapted to the type of mammal. For humans, therefore, use is made of human antibodies or of humanized antibodies made by using techniques that are well known in the art.

The invention also relates to a method of screening a number of compounds with respect to their ability to inhibit the binding of N-AcPGP to a PMN, wherein screening occurs a) by using an assay comprising a competition reaction between a compound E to be assayed and a compound D for the binding to a PMN, wherein compound D is capable of competing with N-acetyl-Pro-Gly-Pro ("N-AcPGP") for binding to a PMN and at equimolar concentrations of the compound D and N-AcPGP, inhibits the binding of N-AcPGP by at least 50%, and at equimolar concentrations of the compound E and compound D, inhibits the binding of D to the PMN by at least 10%, and b) by contacting the compound E with a PMN and selecting a compound E which substantially does not induce activation of the PMN.

This is an efficient manner of selecting compounds E which inhibit the binding of the PGP-comprising signal substance to its receptor on the PMN. In practice it will be preferred to first carry out step a) and then step b).

Suitably compound D is N-R-Pro-Gly-Pro, wherein R is a branched or linear alkyl or acyl group having 1 to 6 carbon atoms, preferably 1 to 2 carbon atoms, such as N-Ac-PGP or N-methyl-PGP.

According to a suitable embodiment the assay in respect to the activation of the PMN comprises measuring the polarization of the PMN.

The polarization can be established in a simple manner, such as described by Haston, W. S. and Shields, J. M. "Neutrophil Leukocyte chemotaxis: a simplified assay for measuring polarizing responses to chemotactic factors". J. Immunol. Methods. 81: 229–237 (1985).

According to a suitable embodiment the inhibition of the binding is established with the aid of flow cytometry.

The inhibition of the binding, and also the activation of the PMN can be established in a simple manner with the aid of flow cytometry.

The invention further relates to a pharmaceutical composition comprising a compound according to the invention or a compound selected with a method according to the invention, as well as a pharmaceutically acceptable carrier or excipient.

The invention also relates to an application of a compound according to the invention, or a compound selected with a method according to the invention, for the preparation of the pharmaceutical composition suitable for the treatment of a chronic inflammatory disease in a mammal, such as a disease belonging to the group comprising chronic inflammatory bowel diseases, rheumatoid arthritis, and other autoimmune diseases, heart diseases that are characterized by an influx of neutrophilic granulocytes, such as heart ischemia, Adult Respiratory Distress Syndrome (ARDS), asthma and lung emphysema.

BRIEF DESCRIPTION OF THE DRAWINGS

The invention will now be explained in more detail with reference to the following examples and with reference to the drawing in which.

PEPTIDE SYNTHESIS

Figure 1:
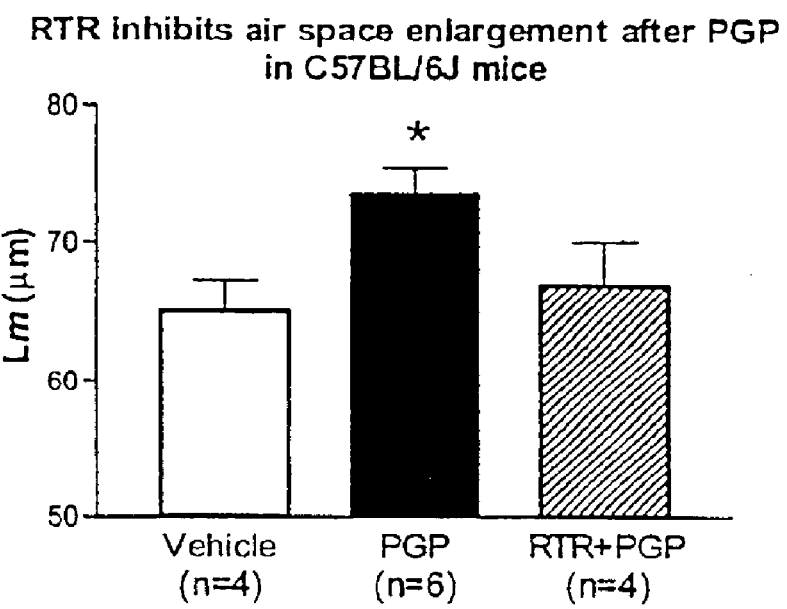
FIG. 1 is a histogram showing the effect of 4-RTR on the dilatation of bronchial tubes.

Peptide synthesis is well established in the art. Peptides may also be obtained commercially as a custom-made product. The following description of the synthesis of 4RTR and N-AcPGP are just respective routes to obtain said compounds.

Preparation of 4RTR

The sequence RTR was chosen using a method described by Blalock (Nature Medicine, 1, p. 876 (1995)). The two glycine residues in 4RTR serve as a spacer. The number of glycine residues may vary (for example, one glycine residue instead of two also gives excellent results) and, indeed, spacers other than glycine may be used. Amino acids may be L or, to have a greater stability against (proteolytic) degradation in vivo, D. The D configuration does not appear to have a significant effect on its ability to bind N-acetylPGP (results not shown).

The RTR tetrameric peptide ((H$_2$N-Arg-Thr-Arg-Gly-Gly)$_2$-Lys)$_2$-Lys-Ala-CONH$_2$), containing laevorotatory (L) RTR sequences, was synthesized using Solid Phase Peptide synthesis following Fmoc methodology on a 9050 Peptide synthesizer from Perceptive Biosystem. This (L)-RTR tetrameric peptide was synthesized starting from a Fmoc-Alanine-PEG-PS resin, with either one or two coupling cycles with Fmoc-K-moc-OH activated with HATU/DIPEA. The following couples were achieved using Fmoc amino acids activated with HATU/DIPEA. The Fmoc deprotection reagent was 1% DBU, 1% Piperidine in dimethylformamide. The peptide was cleaved from the resin by adding 10 ml of trifluoroacetic acid (TFA)/phenol/thioanisol/$H_2O$/ethanedithiol 93/2/2/2/1 and incubated at room temperature from 5 hours. The mixture was filtered and the peptide precipitated in cold ethyl ether. The precipitate was collected and solubilized in $H_2O$ for lyophilization. The peptide was purified by reverse phase high performance liquid chromatography (RP-HPLC), using a Dynamax RP C18 (300×10 mm i.d.), and equilibrated at 3 ml/min using a linear gradient from 5% $CH_3CN$ to 60% $CH_3CN$ in 0.1% TFA in 40 minutes. The fractions containing the peptide were acidified with 1 N HCl to help in the elimination of TFA, and lyophilized. Peptide identity was confirmed by time of flight matrix assisted laser desorption ionization mass spectroscopy. Purity was confirmed by analytical RP-HPLC.

The RTR tetrameric peptide (($H_2$N-d-Arg-d-Thr-d-Arg-Gly-Gly)$_2$-Lys)$_2$-Lys-Ala-$CONH_2$), containing dextrorotatory (D) RTR sequences (only RTR was d confirmation), was synthesized manually starting with 3 g of the Fmoc-Pal-Peg-PS resin with an initial substitution of 0.2 mmol/g of resin. DMF was used as solvent for the coupling steps and the washing steps, while Fmoc was achieved with 1% DBU/2% Piperidine in DMF. Monitoring of the coupling and deprotection steps was conducted using the Kaiser assay. All amino acids were doubly coupled for one hour, using as activating reagents, HOAt for the O-Pentafluorophenyl ester amino acid and HATU/DIPEA for the free acids. An excess of 5 equivalents of amino acid over the resin substitution was used for alanine and the first lysine, 10 equivalents for the second lysine, and 20 equivalents for the following amino acids. The (D)-RTR tetrameric peptide was cleaved from the resins and purified as for the (L)-RTR peptide.

Preparation of N-AcPGP

The dipeptide t-Boc-PG was coupled to Pro-Merrifield resin using the dicyclohexylcarbodiimide/1-hydroxybenzotriazole procedure. After the removal of the N-terminal protection and acetylation using acetic anhydride, the peptide was cleaved from the resin using anhydrous hydrofluoric acid. The product was purified on a silica gel column using chloroform:methanol 90:10 v/v) as the eluent. Homogeneity was confirmed by RP-HPLC on a Vydac C18-analytical column equilibrated at a flow rate of 1.2 ml/min and eluted with a linear gradient from 0% to 30% acetonitrile in water (0.1% trifluoroacetic acid) in 30 minutes. Peptide identity was confirmed by Electrospray Mass Spectrometry (Perkin-Elmer-Sciex API-3). Quantitative amino acid analysis was performed to show the correct ratio of amino acids and to determine the peptide content for calculation of the final concentration.

EXAMPLE 1

Inhibition of Neutrophilia in the Mouse, Induced by PGP-Comprising Compounds

Solutions were prepared of N-Ac-PGP (0.36 mg/ml; $10^{-3}$ M) and N-methyl-PGP (0.32 mg/ml; $10^{-3}$ M) in phosphate-buffered physiological salt (PBS). In an atomizing chamber, 6–8 weeks old Balb/c mice (groups of 4 mice) were subjected for 30 minutes to either N-acetyl-PGP or N-methyl-PGP. Control mice only received PBS. One hour prior to subjection in the atomizing chamber and one hour after the start of subjection each mouse received 50 µl of 1 mg/ml 4RTR. The treatment is outlined in the Table I below.

TABLE I

Outline of treatment:

| group number | pre-treatment | | atomization | | |
|---|---|---|---|---|---|
| n = 4 | PBS | 4RTR | PBS | N-a-PGP | N-m-PGP |
| 1 | + | − | + | − | − |
| 2 | + | − | − | + | − |
| 3 | + | − | − | − | + |
| 4 | − | + | + | − | − |
| 5 | − | + | − | + | − |
| 6 | − | + | − | − | + |

5 hours after the onset of subjection the mice were sacrificed by administering an overdose of Nembutal. After the application of a tracheal canula the lungs were washed with 4 ml PBS. The lung-wash liquid was centrifuged (5 min.; 4° C.; 580 g) and the cell pellet was taken up in 150 µl PBS. The cells were counted under the microscope. To distinguish between neutrophilic and eosinophilic granulocytes and mononuclear cells (haematoxylin/eosin dye, H/E dye: Diff-Quick, Merz & Dade, A.G. Dübingen, Switzerland), the cytospin technique was applied (Buckley, T. L. and Nijkamp, F. P., "Airways hyperreactivity and cellular accumulation in a delayed-type hypersensitivity reaction in the mouse: modulation by capsaicin-sensitive nerves". Am. J. Respir. Crit. Care Med. 149: 400–407 (1994)).

Table II shows that the atomization of N-AcPGP and N-methyl-PGP results in the influx of neutrophilic and eosinophilic granulocytes in the lungs. Pretreatment with 4RTR resulted in a substantially total inhibition of the influx of neutrophilic granulocytes.

TABLE II

Effect of treatment with 4RTR.
The effect of 4RTR treatment on the PGP-induced PMN influx in the mouse lung

| Treatment | Total | Neutros | Eos | Monos |
|---|---|---|---|---|
| PBS/PBS | 30.4 ± 4.3 | 0.6 ± 0.3 | 0.0 ± 0.0 | 29.8 ± 4.2 |
| PBS/N-AcPGP | 49.5 ± 3.1 | 20.1 ± 7.5* | 1.1 ± 0.6 | 28.3 ± 8.6 |
| PBS/N-methylPGP | 46.1 ± 3.2 | 11.9 ± 3.6* | 0.2 ± 0.1 | 33.9 ± 3.4 |
| 4RTR/PBS | 32.6 ± 1.7 | 0.5 ± 0.4 | 0.0 ± 0.0 | 32.1 ± 1.9 |
| 4RTR/N-AcPGP | 26.3 ± 3.3 | 1.3 ± 0.4 | 0.2 ± 0.2 | 24.7 ± 3.2 |
| 4RTR/N-methylPGP | 25.9 ± 3.1 | 0.9 ± 0.3 | 0.0 ± 0.0 | 25.9 ± 3.1 |

Numbers (×$10^4$ cells/ml) are given ± SEM.
*$P < 0.05$, ANOVA

EXAMPLE 2

Induction of Lung Emphysema by N-AcPGP and Inhibition by 4-RTR

On day 0, 2 and 7, two groups C75Bl/6J mice received 30 minutes' treatment with an aerosol (in an atomizing chamber as described in example 1) comprising (i) vehicle (phosphate-buffered physiological salt solution), (ii) N-AcPGP (0.4 mg/ml) or (iii) N-AcPGP (0.4 mg/ml) and 4-RTR (1 mg/ml). 30 Minutes prior to the aerosol, the mice of group (i) and (ii) received intranasal vehicle and the mice of group (iii), 4RTR (1 mg/ml). 24 Hours after the final treatment the first group of mice (i.e. on day 8) exhibited a 2-fold increase of the total number of inflammatory cells in the bronchial-alveolar washing liquid in comparison with the vehicle control (PBS). 4RTR produced approximately a 75% inhibition of this increase. This 4RTR inhibition is specific for N-AcPGP, because 4RTR does not significantly inhibit the increase of the number of cells caused by the bacterial chemotactic peptide FMLP. (see Table III).

TABLE III

4RTR inhibits the increase of cells in the bronchial-
alveolar liquid induced by N-AcPGP in C57B1/6J mice.

| (×10$^5$) | Vehicle | N-AcPGP | 4RTR + NacPGP | 4RTR | FMLP | 4RTR + FMLP |
|---|---|---|---|---|---|---|
| Total number infl. cells | 30 ± 3 | 55 ± 1* | 29 ± 1 | 36 ± 8 | 61 ± 5* | 58 ± 12* |
| Number PMNs | 0.3 ± 0.1 | 11.7 ± 0.8* | 1.2 ± 0.6 | 0.1 ± 0.1 | 10.7 ± 3* | 6.8 ± 1* |

*P < 0.05 compared with vehicle; ANOVA by Dunnett's assay for multiple comparison (n = 3).

On day 21 the mice of the second group (which on day 0, 2, and 7 were treated in the same manner as the mice of the first group), were sacrificed by means of an overdose of anaesthetic (Nembutal) and the lungs were isolated and fixed by filling the lungs with Carnoy's fixative under a liquid pressure of 25 cm. The lungs were prepared for histological analysis. The mean linear intercept (Lm), indicative for alveolar dilatation, was calculated by placing a grid over the illustrations of 5 separate fields (300× magnification) per mouse lung. The total length of the lines was divided by the number of intercepts, resulting in the Lm, providing a measure for the average size of the bronchial volume of the lung.

Treatment with N-AcPGP resulted in a significant increase of the Lm, which was prevented by simultaneous treatment with 4-RTR (see FIG. 1. p<0.05 in comparison with the vehicle. ANOVA succeeded by the assay of Dunnett for multiple comparison). This result was in concurrence with the change in the number of inflammatory cells.

Therefore these results show that 4-RTR has an inhibiting effect on the development of inflammation-related lung emphysema induced by N-AcPGP.

EXAMPLE 3

4-RTR Treatment in a Model of Inflammatory Bowel Disease (IBD) Model

On day 0, the Balb/c mice were sensibilized with dinitrofluorobenzene (DNFB, 0.5% w./vol.), 50 µl being rubbed on the shorn belly and 50 µl on the top of the paws. On day 1 an additional 50 µl DNFB (0.5% w./vol.) was rubbed on the belly of the mice.

On day 5 the mice were challenged with dinitrobenzene sulphonic acid (DNS, 1.2% w./vol., 25 µl rectal; 2 cm deep).

30 Minutes before and 30 minutes after the challenge the mice underwent a rectal treatment (2 cm deep) with PBS or 4-RTR (5 µg/50 µl).

24 Hours after the challenge the results were tallied on the basis of the consistency of the feces, with a tally of 0, 1, or 2 (0=normal, 2=diarrhoea and 1=in between).

Figure 2:
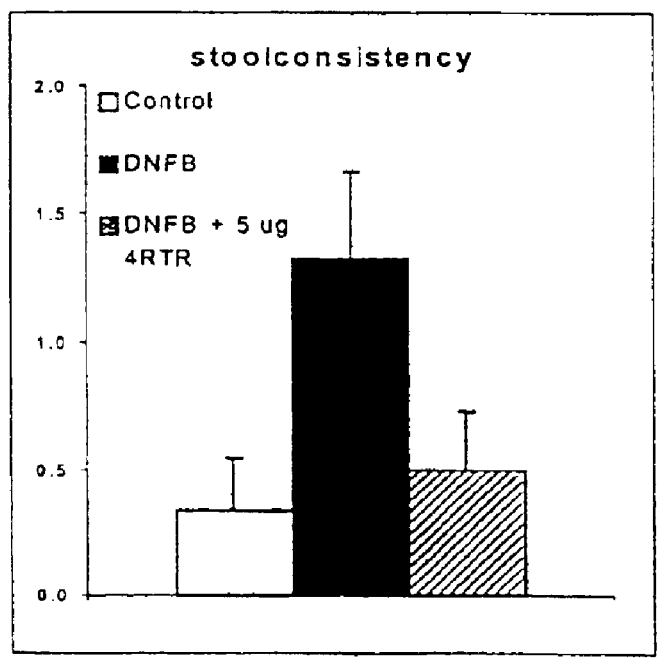
FIG. 2 is a histogram showing the effect of 4-RTR in a model of Inflammatory Bowel Disease.

The results were plotted (FIG. 2) as averages of the group (n=6).

4-RTR (5 µg/50 µl) completely inhibits the development of diarrhoea in the IBD-model.

REFERENCES

1. Ugwo S. O. et al., J. Pharm. Biomed. Anal. Mar; 19(3–4): p. 391–7 (1999);
2. Paradossi G. et al., Biopolymers, Aug.; 50(2): p. 201–9 (1999).

What is claimed is:

1. A method of treating an autoimmune disease in a subject which comprises administering to the subject a therapeutically effective amount of a pharmaceutical composition comprising a peptide consisting of arginine-threonine-arginine (RTR) and/or 4-RTR.

2. The method of claim 1, wherein the autoimmune disease is chronic inflammatory bowel disease.

3. The method of claim 1, wherein the autoimmune disease is rheumatoid arthritis.

4. A method of treating a heart disease that is characterized by an influx of neutrophilic granulocytes in a subject which comprises administering to the subject a therapeutically effective amount of a pharmaceutical composition comprising a peptide consisting of arginine-threonine-arginine (RTR) and/or 4-RTR.

5. The method of claim 4, wherein the heart disease is heart ischemia.

6. A method of treating Adult Respiratory Distress Syndrome (ARDS) in a subject which comprises administering to the subject a therapeutically effective amount of a pharmaceutical composition comprising a peptide consisting of arginine-threonine-arginine (RTR) and/or 4-RTR.

7. The method of claim 6, wherein the Adult Respiratory Distress Syndrome (ARDS) is asthma.

8. The method of claim 6, wherein the Adult Respiratory Distress Syndrome (ARDS) is lung emphysema.

* * * * *